United States Patent
Loescher

(10) Patent No.: US 8,979,812 B2
(45) Date of Patent: Mar. 17, 2015

(54) STOMA PAD/SEAL RING

(75) Inventor: Thomas C. Loescher, Rancho Santa Fe, CA (US)

(73) Assignee: Galmed, Taipei (TW)

( * ) Notice: Subject to any disclaimer, the term of this patent is extended or adjusted under 35 U.S.C. 154(b) by 29 days.

(21) Appl. No.: 13/298,087

(22) Filed: Nov. 16, 2011

(65) Prior Publication Data

US 2012/0130297 A1 May 24, 2012

Related U.S. Application Data

(60) Provisional application No. 61/415,235, filed on Nov. 18, 2010.

(51) Int. Cl.
- A61F 5/44 (2006.01)
- A61F 5/32 (2006.01)
- A61F 5/34 (2006.01)
- A61F 5/443 (2006.01)
- A61F 13/00 (2006.01)

(52) U.S. Cl.
CPC ....... A61F 5/443 (2013.01); *A61F 2013/00978* (2013.01)
USPC .......................................... 604/338; 604/339

(58) Field of Classification Search
CPC .................... A61F 2220/0033; A61F 2220/00; A61F 2230/0004; A61F 5/44; A61F 5/32; A61F 5/34
USPC .................................................. 604/338, 339
See application file for complete search history.

(56) References Cited

U.S. PATENT DOCUMENTS

| | | | |
|---|---|---|---|
| 3,422,817 A | 1/1969 | Mishkin et al. | |
| 4,617,691 A | 10/1986 | Monti et al. | |
| 4,931,045 A * | 6/1990 | Steer | 604/338 |
| 5,058,579 A | 10/1991 | Terry et al. | |
| 5,471,980 A | 12/1995 | Varner | |
| D385,741 S | 11/1997 | Lebenbaum | |
| 5,918,599 A | 7/1999 | Shesol | |
| 6,105,577 A | 8/2000 | Varner | |
| 6,689,111 B2 * | 2/2004 | Mulhauser et al. | 604/332 |
| 6,793,434 B1 | 9/2004 | Olson | |
| 8,469,024 B2 | 6/2013 | Loescher | |
| 2002/0077611 A1 * | 6/2002 | von Dyck et al. | 604/333 |
| 2006/0122595 A1 * | 6/2006 | Farin et al. | 606/45 |
| 2008/0119804 A1 * | 5/2008 | Cline et al. | 604/338 |
| 2009/0318883 A1 * | 12/2009 | Sugahara et al. | 604/298 |

OTHER PUBLICATIONS

Kapi-Gel tracheostoma spacer, Kapitex Healthcare Ltd, Sep. 1, 2010.
The Provox® System Catalog 2010, Atos Medical AB, Aug. 5, 2010.

* cited by examiner

*Primary Examiner* — Tatyana Zalukaeva
*Assistant Examiner* — Sara Sass
(74) *Attorney, Agent, or Firm* — Knobbe, Martens, Olson & Bear LLP

(57) ABSTRACT

A stoma pad configured to cooperate with a fluid handing tube comprises a flexible, resilient, soft annular pad having a generally flat bottom surface and a convex annular wall extending upwardly from the bottom surface, and a circular hole extending through the center of the annular wall and the bottom surface. A stoma pad assembly comprises the stoma pad and a retention, support or holding device for securing the stoma pad on a patient.

19 Claims, 4 Drawing Sheets

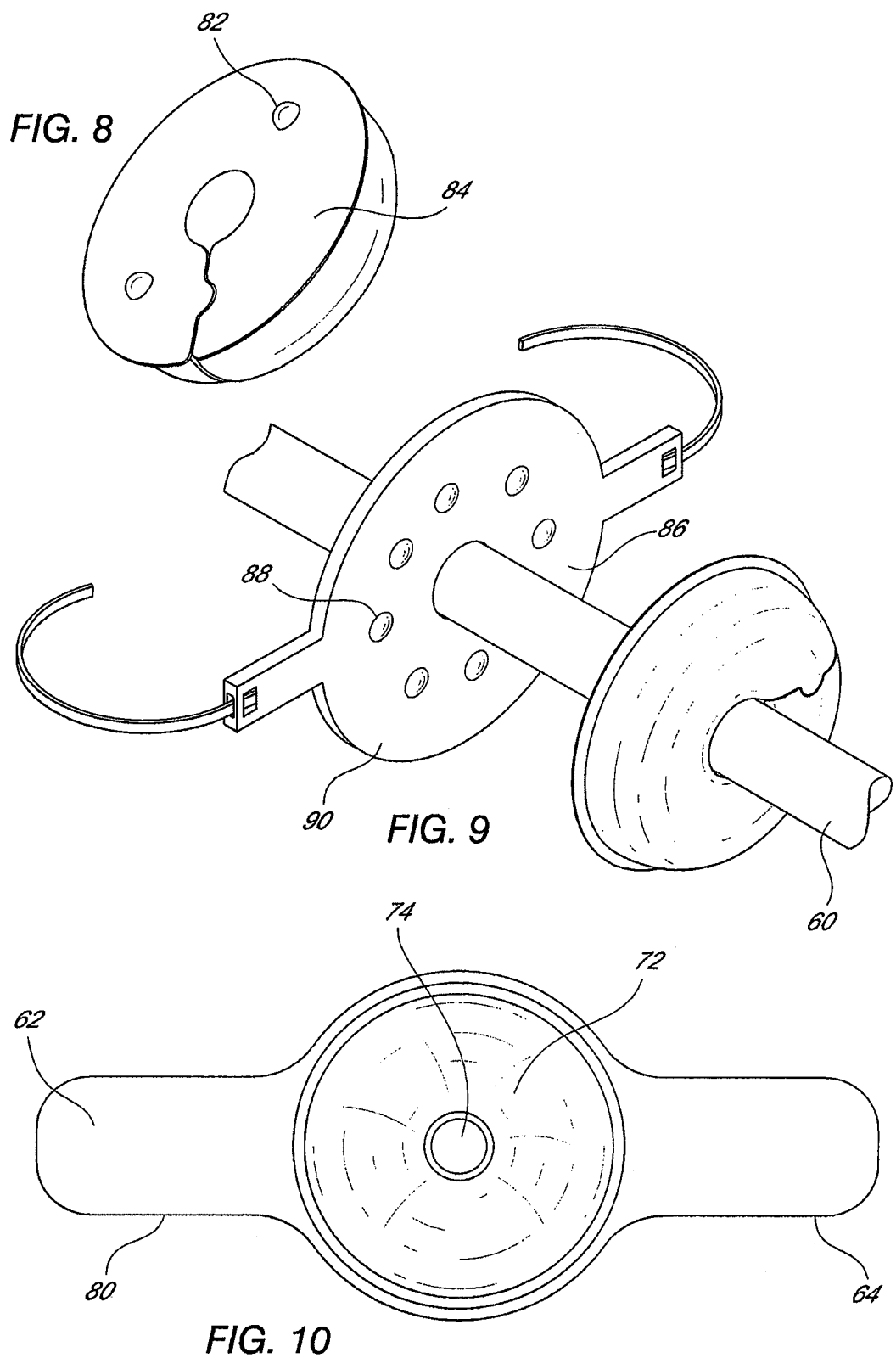

STOMA PAD/SEAL RING

CROSS REFERENCE TO RELATED APPLICATIONS

This application claims priority to U.S. Provisional Patent Application No. 61/415,235 filed Nov. 18, 2010 which is incorporated herein by reference.

BACKGROUND OF THE INVENTION

In addition to tracheostomies typically performed by a surgeon, nurse or paramedic in the patient's throat for inserting a tracheostomy tube or endotracheal tube, stomas or wounds in other body locations may also be intentionally created for inserting a tube to drain bodily fluids or to introduce flushing fluids to the body. In order to support the drain and/or flush tube, a support means or holder device is used for maintaining placement of the tube and securing it adjacent to the body. A stoma/seal ring or pad used in cooperation with the holder device prevents the holder from causing trauma and irritation to the wound and adjacent skin as well as to prevent undue exposure to environmental issues, bacteria, moisture, etc., while maintaining integrity and stabilization of the tube during the continuing patient treatment.

SUMMARY OF THE INVENTION

The stoma pad/seal ring described herein is configured to cooperate with a fluid handling tube inserted into a body wound and comprises a flexible, resilient, gel-like annular pad having a generally flat bottom surface and a convex annular wall extending upwardly from the bottom surface, and a circular hole extending through the center of the annular wall and the bottom surface.

In one embodiment, the annular pad is provided with a slit from the outside surface of the annular wall to the circular hole whereby the circumference of the annular pad and hole can be expanded somewhat via the slit for attaching the pad to the tube and contracted due to its memory retaining resiliency to its original condition. In another embodiment, the single slit between one outside annular wall surface and the center hole is provided with a tongue-in-groove-like recess and flange arrangement for creating a more effective fluid seal. Other features and embodiments will be described further hereinafter.

Embodiments of support member/holding devices for securing the stoma pad/seal ring are also described.

BRIEF DESCRIPTION OF THE DRAWINGS

FIG. 8 is a perspective view of the bottom of another embodiment of the stoma pad showing protuberances or keys for securing the pad with another holder device embodiment;

FIG. 9 illustrates the stoma pad shown in FIG. 8 and a holder device with components for receiving and stabilizing the pad and holder components; and FIG. 10 illustrates a bandage and stoma pad embodiment.

DETAILED DESCRIPTION OF EMBODIMENTS

Figure 1:
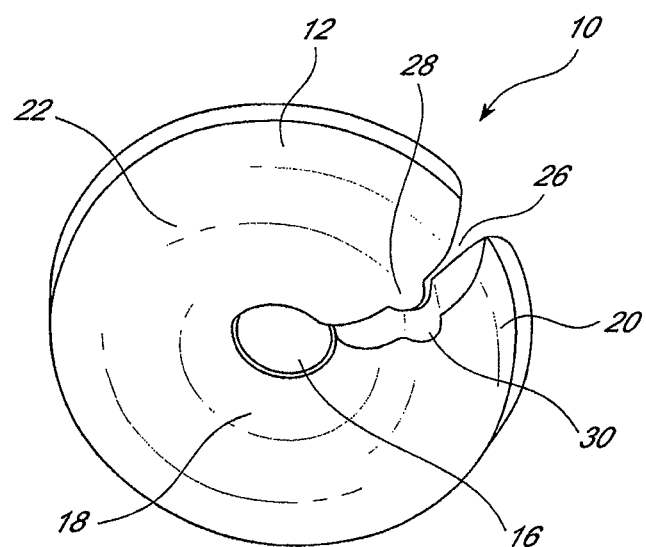
FIG. 1 is a perspective view of the top and side surfaces of the convex annular wall of one embodiment of a stoma pad.

In the embodiment illustrated in FIGS. 1-4, the annular stoma pad/seal comprises a convex annular wall 12, a flat bottom surface 14 and a circular hole 16. The convex annular wall comprises an inside wall surface 18 conforming to and defining the hole 16 and an outside wall surface 20, both of which wall surfaces extend upwardly from the flat bottom surface 14. Connecting the inside and outside wall surfaces is a top surface 22 which extends uniformly between the inside and outside wall surfaces 18 and 20, respectively. In the embodiment shown the connecting top surface 22 is generally convex and extends uniformly between the inside and outside wall surfaces which are generally parallel. However, in other embodiments, either or both the inside and outside wall surfaces may be somewhat angled or offset from 90° along at least a portion of their length toward the upper top connecting convex surface, whereby the convex annular wall is tapered. In such tapered wall embodiments, the thickness of the annular wall will vary accordingly. In one embodiment, the inside/outside wall surfaces as well as the top connecting surface 22 are smooth and uniform.

Figure 2:
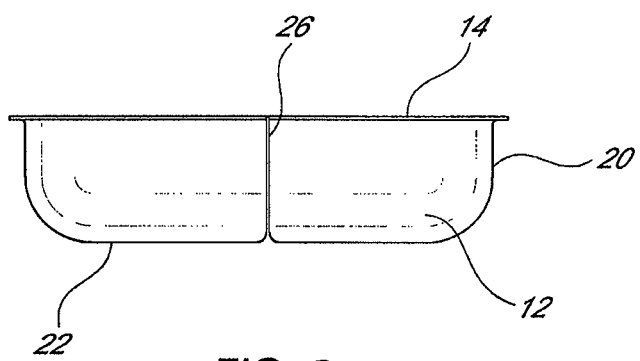
FIG. 2 is a side plan view of one embodiment of a stoma pad.
Figure 3:
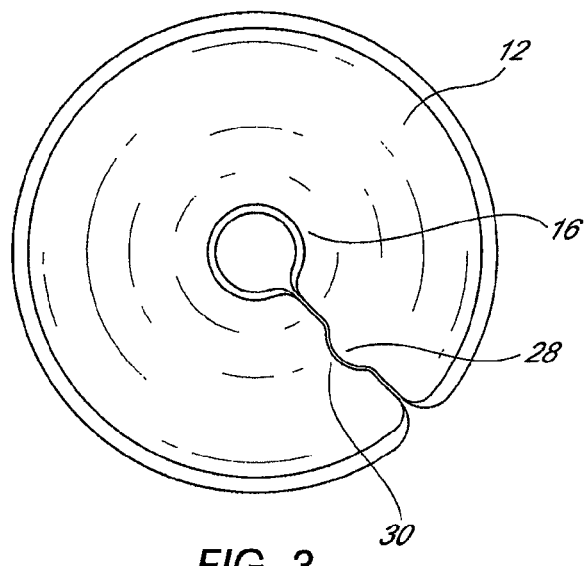
FIG. 3 is a top plan view of one embodiment of a stoma pad.
Figure 4:
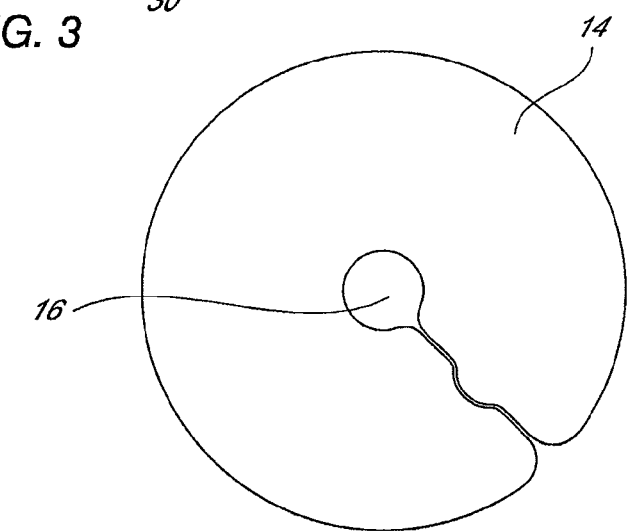
FIG. 4 is a bottom plan view of one embodiment of a stoma pad.

In another embodiment, referring to FIGS. 1-3, a single slit 26 extends through the annular wall between the outside wall surface 20 and the inside wall surface 18 whereby the annular stoma pad can be expanded to allow it to be conveniently secured on a fluid collection or delivery tube without removing the tube from a patient. Thus, the use of such a slit allows convenient and expedient exchange of a stoma pad or replacing any existing pad, gauze, or other device or material protecting the wound while keeping the fluid tube in place for continuing therapy and without unduly traumatizing the wound.

In another embodiment, the slit 26 is provided with a tongue-in-groove type of surface for creating a seal between the two facing slit surfaces. As particularly illustrated in FIGS. 1 and 3, such a feature is shown as a tongue 28 which nests and fits into a recess 30 opposite the tongue. Any other convenient types of securing surfaces and components with other shaped flanges and interlocking or receiving grooves or channels for achieving the same results may be used as understood by those skilled in the art.

Referring again to the illustrated embodiment of the convex annular wall 12 of stoma pad 10, the distance across the convex upper or top connecting surface 22 is greater than the height of either of the inside or outside wall surfaces, which are generally of equal height. The thickness of the annular wall between the inside wall surface 18 and outside wall surface 20 is greater than the height of the annular wall. However, in other embodiments, the thickness of the annular wall and the dimension across the upper connecting surface may be substantially the same as or less than the height of the inside and outside wall surfaces. Moreover, the circumference of the pad at the outer and inner wall surfaces may be varied as desired to accommodate different size wounds as well as different size tubes. Thus, a great variety of different sizes of the pad may be formed and the size of the stoma pad described herein is not to be limited to specific heights or thickness of the annular pad nor to specific inside or outside wall surface circumferences.

In one embodiment, the stoma pad is formed of a very soft, and memory retaining flexible polyurethane or silicon rubber composition. A specific example of one material is polyurethane having a Shore durometer hardness of between about 15 and about 40. Another pad composition comprises a soft silicon gel encased in a thin-flexible, soft polyurethane cover, layer or skin. Such compositions and methods of manufacture of such materials are known to those skilled in the art. Again, the material may be very pliant and flexible whereby the surfaces can conform to surfaces of a holder as well as to securing the tube from passing fluid including air or moisture, etc. as well as for conforming to and stabilizing the wound to which it is compressed. The pad may also be treated with an anti-microbial material such as silver nitrate or other composition capable of releasing antiseptic or resisting and preventing infection of the patient's skin and wound against which the pad rests.

Embodiments of a stoma pad/seal described herein may be used in an assembly which includes a holder for maintaining the pad in place as well as stabilizing the fluid directing tube around which the pad is secured. Observing FIGS. 5, 6 and 7, there is shown one embodiment of a pad (FIG. 5) provided with a groove or channel 56 which extends circumferentially around an outside wall surface 50 between a top pad surface 52 and a bottom surface 54. Channel 56 is formed for accepting a locking ring of a holder for holding the stoma pad in place as discussed in more detail below.

Figure 6:
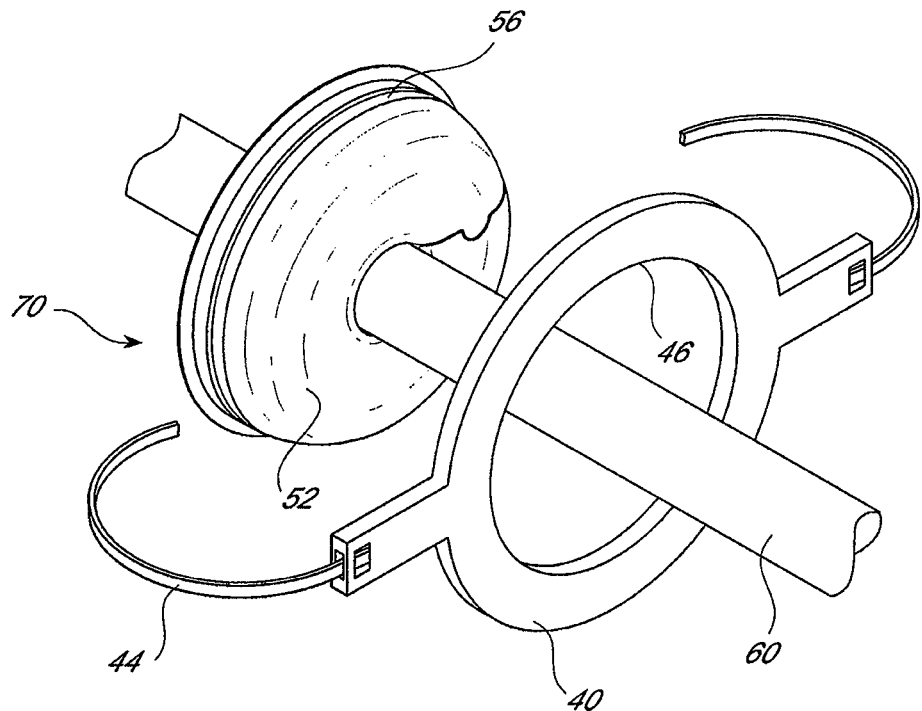
FIG. 6 is a perspective view showing a holder device, a tube, and a stoma pad separated prior to engagement of the stoma pad around a fluid tube [holder device]
Figure 7:
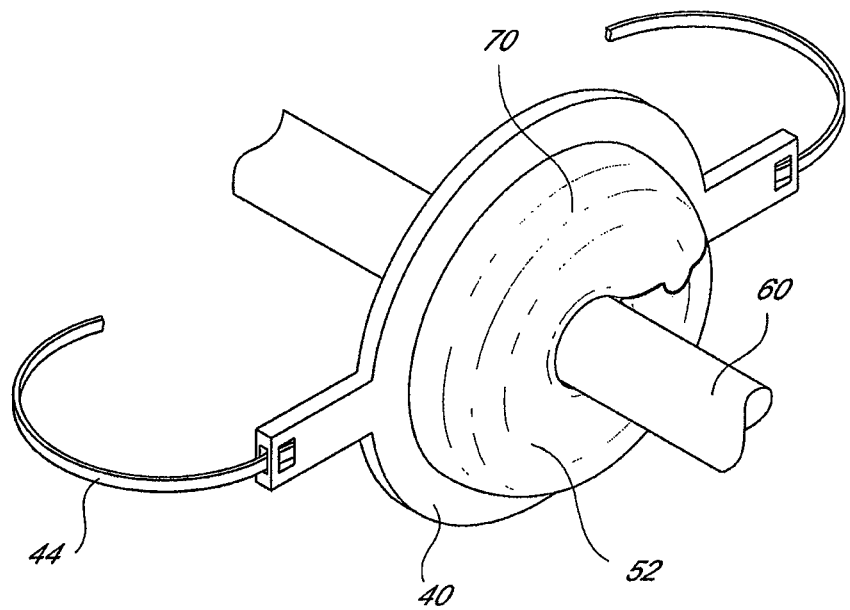
FIG. 7 illustrates the components shown in FIG. 6 assembled for use.

A holder embodiment is shown in FIG. 6. In the embodiment shown, holder 40 is provided with a generally circular opening 46 for receiving or otherwise engaging channel 56 formed on a stoma pad 70. To connect the stoma pad 70 to the holder 40, one simply inserts the flexible and resilient stoma pad through circular hole 46 of the holder 40, whereby channel 56 is received and secured within circular hole 46 of the holder. The assembly of the stoma pad 70 secured in holder 40 with fluid handling tube 60 secured in the stoma pad is illustrated in FIG. 7. The holder embodiment shown includes a strap 44 of sufficient length to be secured around a patient's torso, limb, neck, head or elsewhere on the body during the continued treatment.

FIGS. 8 and 9 illustrate yet another embodiment for securing the stoma pad with a holder. In this embodiment, holder 90 is provided with one or more indentations 88 for receiving protuberances 82 formed on a bottom surface 84 of the stoma pad (FIG. 8). Alternatively, the protuberances 82 may be formed on the surface of the holder and the recesses or depressions formed on the bottom surface of the stoma pad. Any number, shape and/or size of protuberances and indentations may be used.

In yet another embodiment, the stoma pad may be secured to the holder by adhesive, applied to either the bottom stoma pad surface or the pad engaging the holder surface, or both.

FIG. 10 illustrates yet another embodiment for securing a stoma pad on a patient. In this embodiment, a device for securing a stoma pad comprises a flexible adhesive bandage 80 on which stoma pad 72 is secured. Adhesive bandage 80 may be provided with a contact adhesive on upper surface 62 for securing the bottom surface of a stoma pad (see FIGS. 2, 4) to the bandage as well as for securing the bandage on a patient. The bandage is also provided with a hole or orifice to be aligned with opening 74 of the stoma pad. The bandage shown is provided with wings 64 providing expanded adhesive surface area for securing the assembly on a patient. However, the bandage may also be shaped and sized to any desired configuration, and that shown is by way of example only. The bandage material is comprised of any flexible fabric, paper, plastic, etc., such as known and used for bandages.

Figure 5:
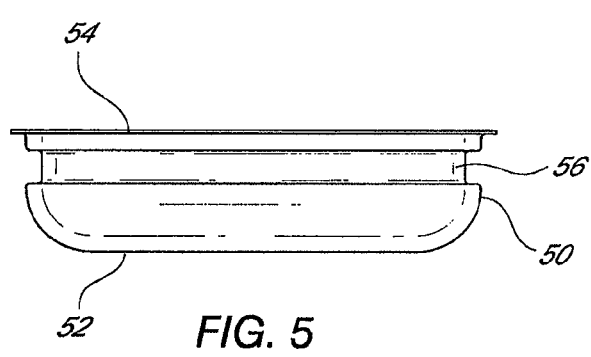
FIG. 5 is a side view of another embodiment of the stoma pad illustrating a circular channel or groove for securing a holder device.

In another embodiment, an adhesive bandage holder, of the type described and shown in FIG. 10, may be used with a stoma pad having a channel 56, as shown in FIG. 5, with the bandage holder secured to the stoma pad, as described regarding the holder of FIG. 6. In such an embodiment, the bandage is provided with a hole of a size sufficient to receive and engage the channel. These as well as other components configured for holding the stoma pad in place and adequately securing the assembly on the patient may be used and those illustrated are by way of example only.

The stoma pad/seal described herein is shaped, formed and configured to allow the pad to act as a seal preventing air and fluid leaks when the stoma to which it is engaged becomes enlarged or stretched as a fluid handling tube as previously described causes expansion of the stoma over time. The soft, flexible and pliable composition of the pad and smooth surface which gently is positioned on the wound is intended to prevent inflammation of the patient's skin adjacent to the stoma, and, unlike gauze pads or the like, does not need to be changed thereby substantially reducing the likelihood of contamination and irritation of the wound during such procedures.

What is claimed is:

1. A stoma pad configured to cooperate with a fluid handling tube inserted into a body wound to seal the body wound, the stoma pad comprising:
    a flexible annular pad having a generally flat bottom surface;
    a thin, flexible cover, the cover forming a convex annular wall extending upwardly from the bottom surface, the cover comprised of a first material;
    a pliant and flexible second material encased in the cover;
    a circular hole extending through the center of the convex annular wall and the bottom surface, wherein the circular hole allows the stoma pad to be secured on the fluid handling tube, wherein a generally circular inside wall surface of the convex annular wall extends upwardly from the bottom surface, defines a circular hole, and is tapered toward the convex annular wall; and
    a slit extending through said convex annular wall and bottom surface, wherein said slit is shaped to form a tongue on one side thereof and a recess on the opposite side thereof for receiving said tongue and forming a fluid seal therebetween.

2. The stoma pad of claim 1 wherein said annular wall comprises the generally circular inside wall surface and an opposite outside wall surface extending upwardly from said bottom surface, a generally convex connecting surface extending between said inside wall surface and said outside wall surface.

3. The stoma pad of claim 2 wherein the distance across said convex connecting surface is greater than the height of either said inside wall surface or said outside wall surface.

4. The stoma pad of claim 2 wherein the thickness of said annular wall is greater than the height of said annular wall.

5. The stoma pad of claim 2 comprising a circular channel extending circumferentially around said outside wall surface.

6. The stoma pad of claim 1 comprising a soft, flexible, resilient plastic material.

7. The stoma pad of claim 1 comprising polyurethane and/or silicon rubber.

8. The stoma pad of claim 1 comprising silicon gel coated with polyurethane.

9. A stoma pad assembly comprising a stoma pad of claim 1 and a stoma pad holding device comprising a flexible bandage secured to the stoma pad.

10. The stoma pad assembly of claim 9 wherein said flexible bandage includes a contact adhesive surface for securing said assembly on a patient.

11. The stoma pad assembly comprising a stoma pad of claim 1 and a stoma pad retention device comprising a generally flat surface for being urged against said generally flat bottom surface of said stoma pad and a hole therethrough aligned with said circular hole through said stoma pad.

12. The stoma pad assembly of claim 11 wherein said retention device comprises a flexible bandage and wherein said generally flat surface thereof comprises a contact adhesive.

13. The stoma pad assembly of claim 11 wherein said generally flat bottom surface of said stoma pad comprises one or more indentations and said generally flat surface of said retention device comprises one or more protuberances for being received in said one or more indentations, respectively.

14. The stoma pad assembly of claim 11 wherein said generally flat surface of said retention device comprises one or more indentations and said generally flat bottom surface of said stoma pad comprises one or more protuberances for being received in said one or more indentations.

15. The stoma pad assembly of claim 9, comprising a stoma pad retention device having a substantially circular hole therein, the circular edge of said hole received in a circular channel of said stoma pad.

16. The stoma pad assembly of claim 11 including a fluid handling tube extending through said stoma pad hole and said retention device hole.

17. The stoma pad assembly of claim 12 including a fluid handling tube extending through said stoma pad hole and said retention device hole.

18. The stoma pad assembly of claim 11 wherein said stoma pad is secured to said retention device with adhesive.

19. A stoma pad configured to cooperate with a fluid handling tube inserted into a body wound to seal the body wound, the stoma pad comprising:
- a flexible annular pad having a generally flat bottom surface;
- a thin flexible cover forming a convex annular wall extending upwardly from the bottom surface, the cover comprised of a first material;
- a pliant and flexible second material encased in the cover;
- a circular hole extending through the center of the annular wall and the bottom surface, wherein the circular hole allows the stoma pad to be secured on the fluid handling tube; and
- a slit extending through said convex annular wall and bottom surface, wherein said slit is shaped to form a tongue on one side thereof and a recess on the opposite side thereof for receiving said tongue and forming a fluid seal therebetween.

* * * * *

UNITED STATES PATENT AND TRADEMARK OFFICE
CERTIFICATE OF CORRECTION

PATENT NO.        : 8,979,812 B2
APPLICATION NO.   : 13/298087
DATED             : March 17, 2015
INVENTOR(S)       : Thomas C. Loescher It is certified that error appears in the above-identified patent and that said Letters Patent is hereby corrected as shown below:

On the Title Page (item 73, Assignee), Change "Galmed Taipei (TW)" to --Galemed Taipei (TW)--.

Signed and Sealed this
Twenty-third Day of August, 2016

Michelle K. Lee
*Director of the United States Patent and Trademark Office*